US010485521B2

(12) United States Patent
Harrell

(10) Patent No.: US 10,485,521 B2
(45) Date of Patent: Nov. 26, 2019

(54) METHOD FOR OBTAINING STERILE HUMAN AMNIOTIC FLUID AND USES THEREOF

(71) Applicant: Carl Randall Harrell, Tarpon Springs, FL (US)

(72) Inventor: Carl Randall Harrell, Tarpon Springs, FL (US)

(73) Assignee: MAM Holdings of West Florida, L.L.C., Tarpon Springs, FL (US)

( * ) Notice: Subject to any disclaimer, the term of this patent is extended or adjusted under 35 U.S.C. 154(b) by 1288 days.

(21) Appl. No.: 14/508,578

(22) Filed: Oct. 7, 2014

(65) Prior Publication Data
US 2015/0025366 A1 Jan. 22, 2015

Related U.S. Application Data

(63) Continuation-in-part of application No. 14/275,086, filed on May 12, 2014, now abandoned.
(Continued)

(51) Int. Cl.
*A61M 1/00* (2006.01)
*A61B 10/00* (2006.01)
(Continued)

(52) U.S. Cl.
CPC ........ *A61B 10/0048* (2013.01); *A61B 8/0841* (2013.01); *A61L 2/081* (2013.01);
(Continued)

(58) Field of Classification Search
CPC ........ A61M 1/0011; A61M 2202/0437; A61M 2202/0494; C12N 5/0605; A61B 10/0048
(Continued)

(56) References Cited

U.S. PATENT DOCUMENTS 3,752,158 A * 8/1973 Kariher ................ A61M 1/0011
604/133
5,015,369 A * 5/1991 Romine ................. A61M 1/30
210/136
(Continued)

FOREIGN PATENT DOCUMENTS

WO 2004026244 4/2004
WO 2006091546 8/2006

OTHER PUBLICATIONS

Cianfarani, et al., "Placement growth factor in diabetic wound healing altered expression and therapeutic potential", Am J Pathol., 169(4):1167-82 (2006).
(Continued)

*Primary Examiner* — Andrew J Mensh
(74) *Attorney, Agent, or Firm* — Pabst Patent Group LLP

(57) ABSTRACT

Provided herein is a method for sterilely filtering amniotic fluid from selected caesarean sections of an individual. The amniotic fluid is first centrifuged at 5,000 to 10,000 rpm for 30 to 60 minutes and filtered through filters with about 5 to about 10 μm pore size. Next, the fluid is sequentially filtered through a series of membrane filters with the pore sizes 1 μm and 0.45 or/and 0.2 μm. The filtrate is then aseptically transferred to and sealed in syringes or vials. The fluid is subsequently lyophilized to obtain the lyophilisate of amniotic fluid. Amniotic fluid is reconstituted by adding sterile water to the lyophilisate, and the reconstituted fluid is used for wound healing, cosmetic, orthopedic or ophthalmic applications, particularly for the treatment of dry eyes.

20 Claims, 10 Drawing Sheets

Related U.S. Application Data

(60) Provisional application No. 61/821,868, filed on May 10, 2013.

(51) Int. Cl.
*A61B 8/08* (2006.01)
*A61L 2/08* (2006.01)
*A61B 10/02* (2006.01)

(52) U.S. Cl.
CPC ............ *A61L 2/087* (2013.01); *A61M 1/0011* (2013.01); *A61B 10/0233* (2013.01); *A61B 10/0283* (2013.01); *A61M 2202/0437* (2013.01); *A61M 2202/0494* (2013.01)

(58) Field of Classification Search
USPC ........................................................ 604/319
See application file for complete search history.

(56) References Cited

U.S. PATENT DOCUMENTS

| | | | |
|---|---|---|---|
| 5,219,576 A | 6/1993 | Chu | |
| 5,436,135 A | 7/1995 | Tayot | |
| 5,698,228 A | 12/1997 | Takai | |
| 5,997,896 A | 12/1999 | Carr, Jr. | |
| 7,871,646 B2 | 1/2011 | Ghinelli | |
| 7,928,280 B2 | 4/2011 | Hariri | |
| 8,372,439 B2 | 2/2013 | Daniel | |
| 2004/0057938 A1 | 3/2004 | Ghinelli | |
| 2004/0093046 A1 | 5/2004 | Sand | |
| 2005/0079147 A1 | 4/2005 | Delaey | |
| 2008/0181935 A1 | 7/2008 | Bhatia | |
| 2008/0181967 A1* | 7/2008 | Liu | A61K 35/44 424/583 |
| 2008/0286378 A1* | 11/2008 | Behrens | A61K 35/50 424/528 |
| 2009/0054350 A1* | 2/2009 | Tayot | C07K 14/78 514/6.9 |
| 2010/0318048 A1 | 12/2010 | Hoefinghoff | |
| 2011/0269667 A1 | 11/2011 | Shoseyov | |
| 2013/0086877 A1* | 4/2013 | Kori | B01D 46/0024 55/482 |

OTHER PUBLICATIONS

Durham, et al., "Preliminary evaluation of vibriolysin, a novel proteolytic enzyme composition suitable for the debridement of burn wound eschar.", J Burn Care Rehabil., 14,(5):544-51 (1993).
Kirker, et al., "Glycosaminoglycan hydrogel films as bio-interactive dressings for wound healing", Biomaterials, 23(17):3661-71 (2002).

\* cited by examiner

METHOD FOR OBTAINING STERILE HUMAN AMNIOTIC FLUID AND USES THEREOF

CROSS-REFERENCE TO RELATED APPLICATIONS

This application is a continuation-in-part of pending non-provisional application U.S. Ser. No. 14/275,086, filed May 12, 2014, which claims benefit of priority under 35 U.S.C. § 119(e) of provisional application U.S. Ser. No. 61/821,868, filed May 10, 2013, now abandoned, the entirety of both of which are hereby incorporated by reference.

BACKGROUND OF THE INVENTION

Field of the Invention

The present invention relates generally to the fields of sterile obtention of amniotic fluid and isolation of biomolecules from amniotic fluid. More specifically, the present invention relates to a method to obtain cell free, biologically active and sterile filtered amniotic fluid by high speed centrifugation and membrane filtration.

Description of the Related Art

Within the uterus of a pregnant woman, a growing fetus is surrounded and cushioned by amniotic fluid, a watery liquid within the amnion. Amniotic fluid is one of the main samples used for the medical examination of the pregnant woman and her fetus.

For gathering information about the fetus's health and development, particularly about the possibility of premature birth, amniotic fluid infection, fetal inflammation and infection, fetal damage, fetal maturity, fetal diseases and chromosomal abnormalities, and component analysis of amniotic fluid, amniocentesis (transabdominal amniotic fluid collection) is carried out by inserting a thin, hollow needle through the abdomen into the uterus and taking a small sample of amniotic fluid. Currently, abdominal puncture with a needle for collecting amniotic fluid from the uterus is used for various amniotic fluid tests including the identification of fetal abnormality and amniotic fluid infection. The insertion of the needle, however, entails the risk of complications and medical accidents, causing anxiety and pain to the pregnant woman.

Traditionally, during a Caesarean section, after cutting through the uterus, the amniotic fluid will be suctioned away and discarded to make a bit more room. Amniotic fluid contains cells, electrolytes, growth factors, carbohydrates, lipids, proteins, amino acids, lactate, pyruvate, enzymes and hormones. Amniotic fluid is also a source of stem cells which ideally should be isolated and separately cultivated for cell therapy purposes. While amniotic fluid cells can be obtained from a small amount of fluid during amniocentesis, these amounts are insufficient for a larger scale harvesting of biomolecules or culturing of the stem cells comprising amniotic fluid. Many authors have published that the biological activity of amniotic fluid in many medical applications is the consequence of the presence of the cells, particularly stem cells (Bhattacharya N. Stubblefield P., "Regenerative Medicine Using Pregnancy-Specific Biological Substances" Springer ed. 2011).

Thus, there is a recognized need in the art for an improved means for obtaining sterile amniotic fluid for use in research and the development of therapeutic products. Particularly, the prior art is deficient in methods for obtaining sterile human amniotic fluid with minimal or no risk to a pregnant woman or fetus by collecting the amniotic fluid prior to an elective Caesarean section. Also the prior art is deficient in methods for obtaining sterile human amniotic fluid devoid of cells which may create unwanted reactions due to their allogenic characters on the patients to be treated. The present invention fulfills this longstanding need and desire in the art to improve the safety of amniotic fluid in its medical uses.

SUMMARY OF THE INVENTION

The present invention is directed to methods of obtaining sterilely filtered human amniotic fluid from an individual. This method comprises the steps of obtaining sterile human amniotic fluid from an individual, removing cells, large particles and other undissolvables from said human amniotic fluid by high speed centrifugation, followed by membrane filtration. The first step is to centrifuge the amniotic fluid in swing out buckets adapted to swing out rotors or other centrifugation bottles in angle rotors at about 5,000 rpm to about 10,000 rpm for about 30 minutes to about 60 minutes. The supernatant is then filtered using filters with a pore size of about 5 µm to about 10 µm to obtain the first filtrate, then filtering said first filtrate through filters with a pore size of about 1.0 µm to obtain a second filtrate, filtering the second filtrate through filters with the pore size of 0.45 µm or/and 0.2 µm to obtain a sterilely filtered amniotic fluid. In case of a final membrane filtration limited to 0.45 µm, it is preferable to repeat a second filtration on a second 0.45 µm membrane, to increase the sterility assurance level. The sterile amniotic fluid retains the growth factors from the raw amniotic fluid. In this method, the first centrifugation step may be replaced by depth filtration through available filtration systems, however this option is not preferred because it leads to important volume losses and undesirable adsorption of growth factors by the filtration media.

The present invention is further directed to a kit containing tools to obtain sterilely filtered human amniotic fluid from an individual, comprising a three-way stopcock, a sterile blunt tip needle aseptically attached to said three-way stopcock, a luer lock syringe aseptically connected to said three-way stopcock, a sterile tubing aseptically connected to said three-way stopcock, a collection container or a collection container comprising a pump with suction device connected with said sterile tubing, a set of filters having a pore size of about 5 µm to about 10 µm, a set of capsule or cartridge filters having a pore size of about 1 µm, a set of capsule or cartridge filters having a pore size of about 0.45 µm or 0.2 µm, a set of sterile syringes or vials to store said sterile filtered amniotic fluid and operating instructions on using the kit to obtain sterilely filtered human amniotic fluid from an individual.

The present invention is further directed to a freeze-dried formulation of amniotic fluid to improve the stability of its growth factors and other peptide hormones. Contrary to the liquid formulation of amniotic fluid, the dried formulation of this invention does not need a cold chain with dry ice or other complex cooling systems, thus facilitating and minimizing the cost of its commercial distribution. The lyophilisate of amniotic fluid is in form of powder. The lyophilisate of amniotic fluid may be used for wound healing, cosmetic, orthopedic, ENT or ophthalmic applications, particularly for the treatment of dry eyes or dry noses.

Other and further aspects, features, and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention, as well as others that will become clear, are attained and can be understood in detail, more particular descriptions of the invention briefly summarized above may be had by reference to certain embodiments thereof that are illustrated in the appended drawings. These drawings form a part of the specification. It is to be noted, however, that the appended drawings illustrate preferred embodiments of the invention and therefore are not to be considered limiting in their scope.

DETAILED DESCRIPTION OF THE INVENTION

Figure 1A:
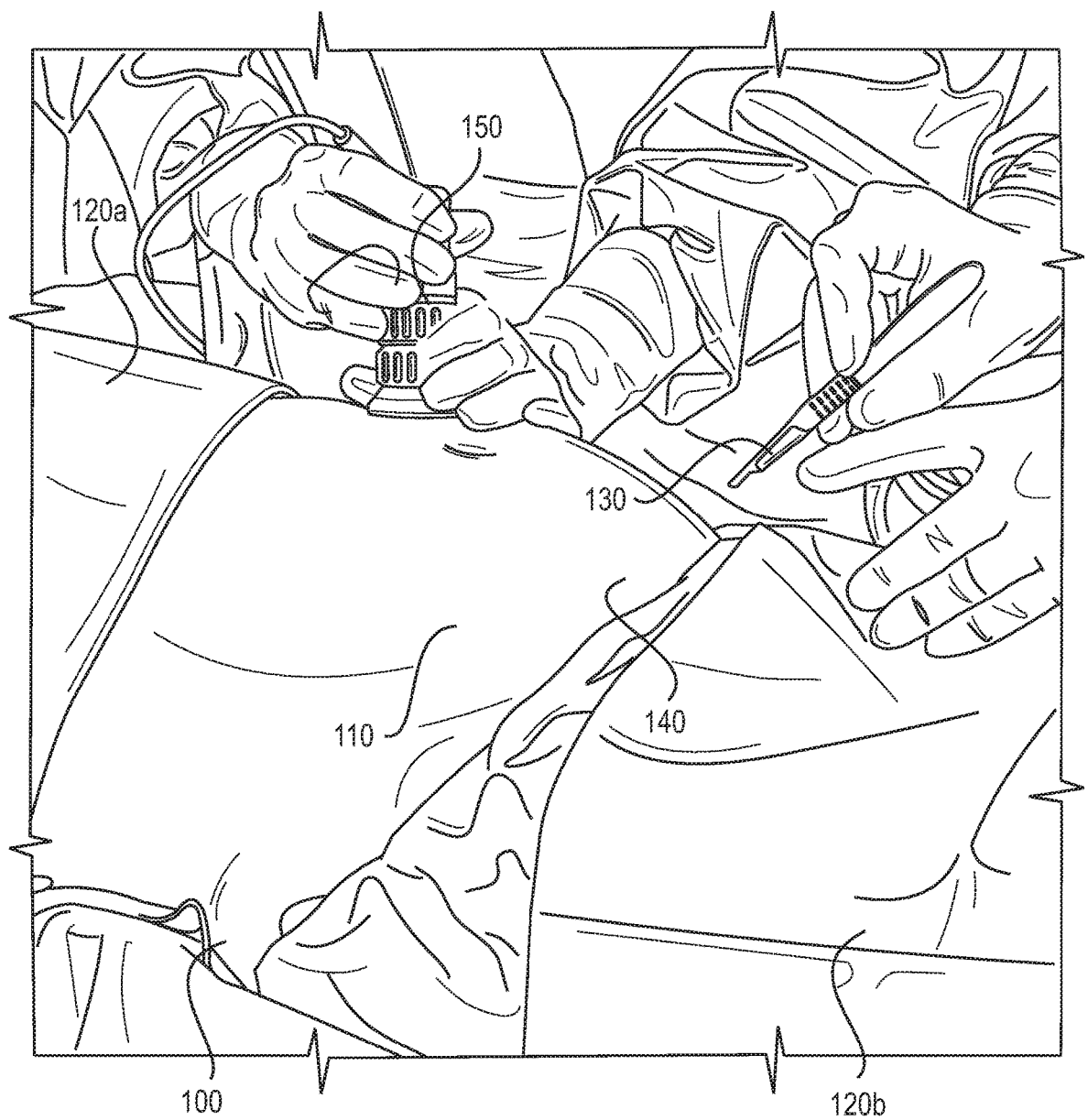
FIGS. 1A-1B depict the surgical set-up and patient from whom amniotic fluid can be collected.

As used herein in the specification, "a" or "an" may mean one or more. As used herein in the claim(s), when used in conjunction with the word "comprising", the words "a" or "an" may mean one or more than one.

As used herein "another" or "other" may mean at least a second or more of the same or different claim element or components thereof. Similarly, the word "or" is intended to include "and" unless the context clearly indicates otherwise. "Comprise" means "include."

As used herein, the term "about" refers to a numeric value, including, for example, whole numbers, fractions, and percentages, whether or not explicitly indicated. The term "about" generally refers to a range of numerical values (e.g., +/−5-10% of the recited value) that one of ordinary skill in the art would consider equivalent to the recited value (e.g., having the same function or result). In some instances, the term "about" may include numerical values that are rounded to the nearest significant figure.

In one embodiment of the present invention, there is provided a method for obtaining sterilely filtered human amniotic fluid, comprising the steps of obtaining sterile human amniotic fluid from a woman, removing cells, large particles and other undissolvables from said human amniotic fluid by high speed centrifugation to obtain clarified amniotic fluid, filtering said clarified amniotic fluid through filters having a pore size of about 5 µm to about 10 µm to obtain a micron filtrate, filtering said micron filtrate through filters with a pore size of about 1.0 µm to obtain a second filtrate, filtering the filtrate through submicron filters with the pore size of 0.45 µm or/and 0.2 µm to obtain the sterilely filtered amniotic fluid.

In this embodiment, the woman is undergoing a pre-caesarian surgical method, and the step of obtaining the sterile human amniotic fluid comprise the steps of turning on a ultrasound device to provide guidance for the whole process of obtaining human fluid from said woman, inserting a blunt tip needle into the amniotic sac of said individual, attaching said blunt tip needle to a three-way stopcock, connecting a Luer lock syringe to said three-way stopcock, connecting a first end of a length of sterile tubing with said three-way stopcock, and collecting sterilely said amniotic fluid through the blunt tip needle and sterile tubing into a collection container.

In this embodiment, the sterile collection container comprises a pump with a suction device. The suction device is a low suction device or a spring loaded low suction device. The suction device is fluidly connected to an internal balloon. This embodiment further comprising manually pumping up the internal balloon in the sterile collection container using the low suction device to allow a low-level suction and collection of the amniotic fluid.

Also in this embodiment, the step of removing cells, large particles and other undissolvables from said human amniotic fluid comprises a first step of centrifuging or depth filtering said human amniotic fluid. The human amniotic fluid is centrifuged at about 5,000 rpm to about 10,000 rpm for about 30 minutes to about 60 minutes. In this embodiment the filters of about 5 µm to about 10 µm used for the first filtration are cellulose ester filters, glass fiber filters, nylon capsule filters or nylon cartridge filters. The filters with the pore size of 1.0 µm are capsule filters or cartridge filters. The filters with the pore size of 1.0 µm are poly ether sulfone, poly vinylidene fluoride or cellulose acetate 1 membrane filters. The filters with the pore size of 0.45 µm or 0.2 µm are capsule filters or cartridge filters. The filters with the pore size of 0.45 µm or 0.2 µm are poly ether sulfone membrane filters, poly vinylidene fluoride or cellulose acetate membrane filters.

Also in this embodiment, the sterilely filtered human amniotic fluid contains growth factors. The growth factors are human growth hormone, transforming growth factor beta 1, vascular endothellal growth factor, epidermal growth factor, transforming growth factor beta 3, and growth differentiation factor 11 or combinations thereof.

In this embodiment of the present invention, the method for obtaining sterile amniotic fluid further comprises the step of lyophilizing said sterile amniotic fluid to obtain a lyophilisate thereof. The method further comprises irradiating said lyophilisate by e-beam irradiation or gamma ray irradiation to reinforce the sterility.

In yet another embodiment of the present invention, there is provided a lyophilized human fluid comprising said lyophilisate produced by the method of described supra. In another embodiment of the present invention, there is provided a pharmaceutical formulation used for wound healing, cosmetic orthopedic or ophthalmic applications, comprising the lyophilized human amniotic fluid and sterile water.

In yet another embodiment of the present invention, there is provided a kit of necessary tools to obtain sterilely filtered human amniotic fluid from a woman, comprising a three-way stopcock, a sterile blunt tip needle aseptically attached to said three-way stopcock, a luer lock syringe aseptically connected to said three-way stopcock, a sterile tubing aseptically connected to said three-way stopcock, a collection container or a collection container comprising a pump with suction device connected with said sterile tubing, a set of filters having the pore size of about 5 µm to about 10 µm, a set of capsule or cartridge filters having the pore size of about 1 µm, a set of capsule or cartridge filters having the pore size of about 0.45 µm or 0.2 µm, a set of sterile syringes or vials to store said sterile filtered amniotic fluid and operating instructions on using the kit to obtain sterilely filtered human amniotic fluid. The filters having the pore size of from about 5 µm to about 10 µm and said capsule or cartridge filters are made from cellulose ester, glass fiber or nylon.

In one embodiment of the present invention there is provided a method of obtaining sterile human amniotic fluid from woman, comprising the steps of inserting a blunt tip needle into the amniotic sac of said woman; attaching the blunt tip needle to a three-way stopcock; connecting a Luer lock syringe to the three-way stopcock; connecting a first end of a length of sterile tubing with the three-way stopcock; and collecting sterilely said amniotic fluid through the blunt tip needle and sterile tubing into a collection container. In this embodiment and any aspects thereof collecting of the amniotic fluid may be performed under ultrasound guidance.

In this embodiment the sterile collection container may comprise a pump with a suction device. In one aspect of this embodiment suction device may be a low suction device or spring loaded low suction device. In another aspect the suction device may be fluidly connected to an internal balloon. Further to this aspect the method comprises manually pumping up the internal balloon in the sterile collection container using the low suction device to allow a low-level suction and collection of the amniotic fluid. In yet another aspect the sterile collection container may comprise an inlet. Further to this particular aspect the method comprises connecting a second end of the tubing to the inlet of the sterile collection container.

In yet another aspect of this embodiment the sterile collection container may comprise a vent having a cap.

Provided herein is a process for obtaining sterile human amniotic fluid in quantity and the human amniotic fluid so collected. A collection procedure is performed in a sterile operating room environment during an elective C-section.

Utilizing the incision site immediately prior to performing the C-section and with ultrasound guidance to protect the fetus and mother provides a minimal or no risk environment for collection. Collection is achieved via a low level suction established within a collection container and/or via gravity. The collected sterile amniotic fluid contains biomolecules and other biomaterials, such as growth factors and stem cells which provide raw starting materials for the development of therapeutics. The collected sterile amniotic fluid also can be filtered for such biomolecules and biomaterials.

A collection system for the sterile collection of amniotic fluid generally comprises fluid collection components and a fluid container component. The collection system is assembled such that amniotic fluid is drawn from a pregnant woman through the fluid collection components, such as a needle and tubing combination, to the container component. The container component comprises a means for pumping up an internal balloon to generate a low level suction to improve flow of the amniotic fluid.

The present invention describes several ways by which a person having ordinary skill in this art could process sterile products collected in amniotic fluid by centrifugation and filtration. Typically, after high speed centrifugation one would perform filtration with 5 to 10 µm filters (low protein binding filter) to complete the removal of cells and large particles. Submicron filtration would then be conducted with 1 µm or/and 0.45 µm or/and 0.2 µm filters (low protein binding filter), two in a series connection, to remove gross contaminates. Under this condition, soluble growth factors will pass through this filter to achieve a semi-sterile condition, very low bioburden counts. If under a strict aseptic operation condition, a $10^{-3}$ sterility assurance level could be achieved.

Further, a $10^{-6}$ sterility assurance level could be achieved by submicron filtration to be conducted with a 0.22 µm filter (low protein binding filter) at the end and sterile packaging to achieve a sterile product. One would monitor the filtrate after each filtration step to determine which components were removed and then to determine which process to use to achieve the desirable product.

Using the methodology described herein, it is possible to filter the amniotic fluid. One may use membrane filters comprising or made of hydrophilic polyethersulphone (PES) to filter protein solutions. Filter disks for small volumes and different sizes of cartridges for larger volumes such 1 liter and more. Hydrophobic membranes like PTFE which are designed for liquids devoid of proteins should not be used. Start with centrifugation at 5000 to 8000 rpm for at least 30 minutes. Next, the supernatant is filtered with a prefilter to remove residual protein aggregates and precipitates in suspension (AP20 can be used). If one directly uses a 0.6/0.2 µm filter, after prefiltration, one may experience slow filtration rates and the flow may stop too quickly. It may be desirable to make intermediate filtration steps using 1.2 µm and 0.8 µm membranes. Typically, a final filtration through 0.2 µm is necessary to get the best sterility assurance level and produce a sterile amniotic fluid for injections. The final filtrate can be stored in frozen condition at about −20° C. to about −80° C. for long term storage. In addition, the sterilely filtered amniotic fluid may be distributed in vials equipped with special rubber stoppers for sterile lyophilization.

The lyophilization is carried out in a sterile environment. The rubber stoppers on the vials are then automatically pushed down in the freeze dryer to definitively close them. Finally an aluminum cap is sealed on each vial to protect its sterile content. In such a lyophilized state, the amniotic fluid may be stored at +4° C. or room temperature for at least one year without decrease of its biological activity. For its medical use, the sterile amniotic fluid may be reconstituted by adding the initial volume of sterile water to the powder in order to restore a transparent and homogeneous physiological liquid.

As described below, the invention provides a number of advantages and uses, however such advantages and uses are not limited by such description. Embodiments of the present invention are better illustrated with reference to the Figure(s), however, such reference is not meant to limit the present invention in any fashion. The embodiments and variations described in detail herein are to be interpreted by the appended claims and equivalents thereof.

Figure 1B:
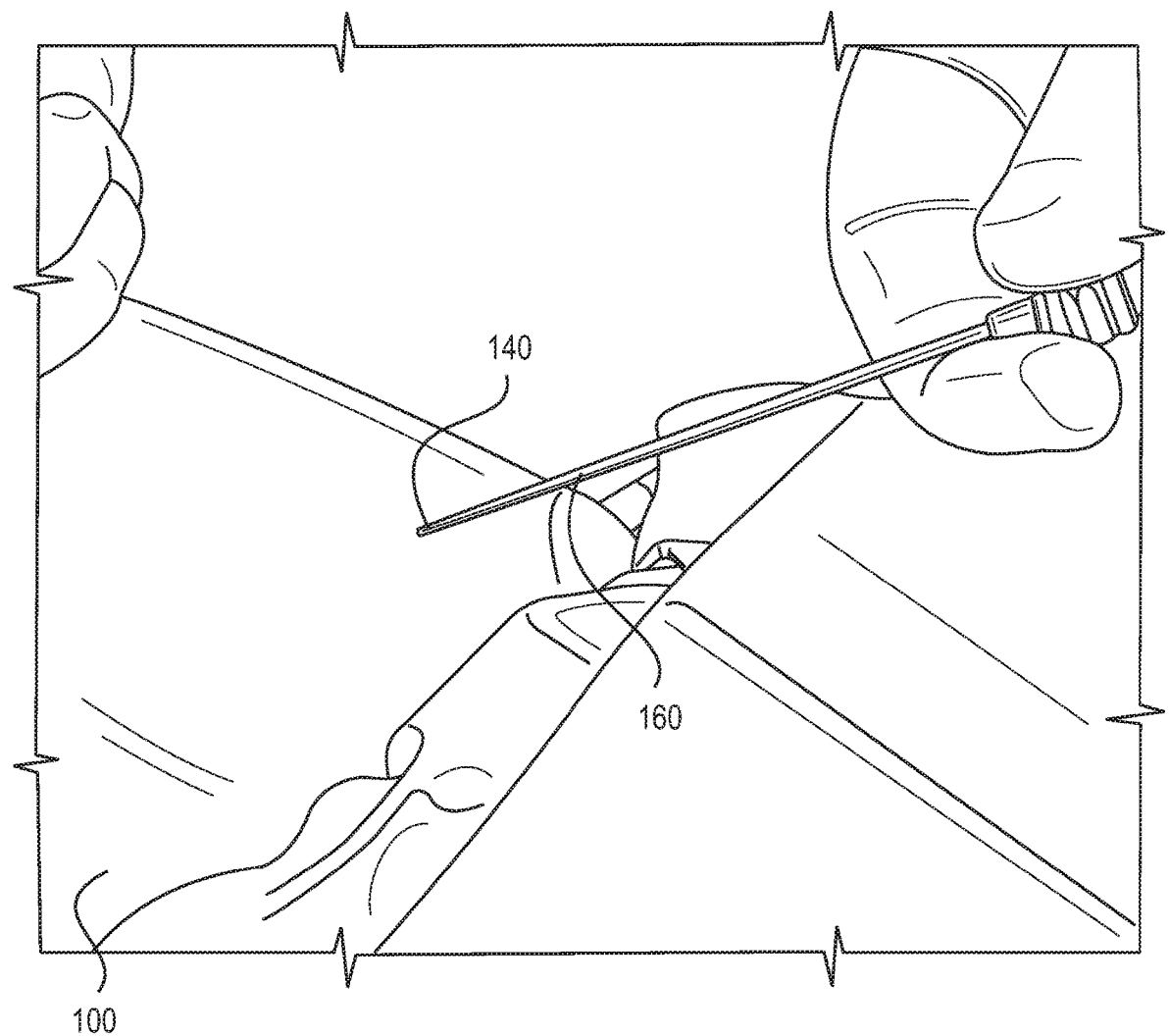

FIG. 1A shows a pregnant patient 100 prepped for a Caesarean section (C-section). The abdomen 110 is cleaned and prepped and the patient is draped at 120a,b as well-known and standard in the art. A number 15 scalpel blade 130 is used at the site of the future C-section incision at 140 to penetrate the dermis. Simultaneously, an ultrasound 150 is performed to protect the fetus and the mother. FIG. 1B illustrates how a blunt tip needle 160, to avoid any blood vessel penetration or damage to fetus or mother 100, is inserted at the incision site 140.

Figure 2A:
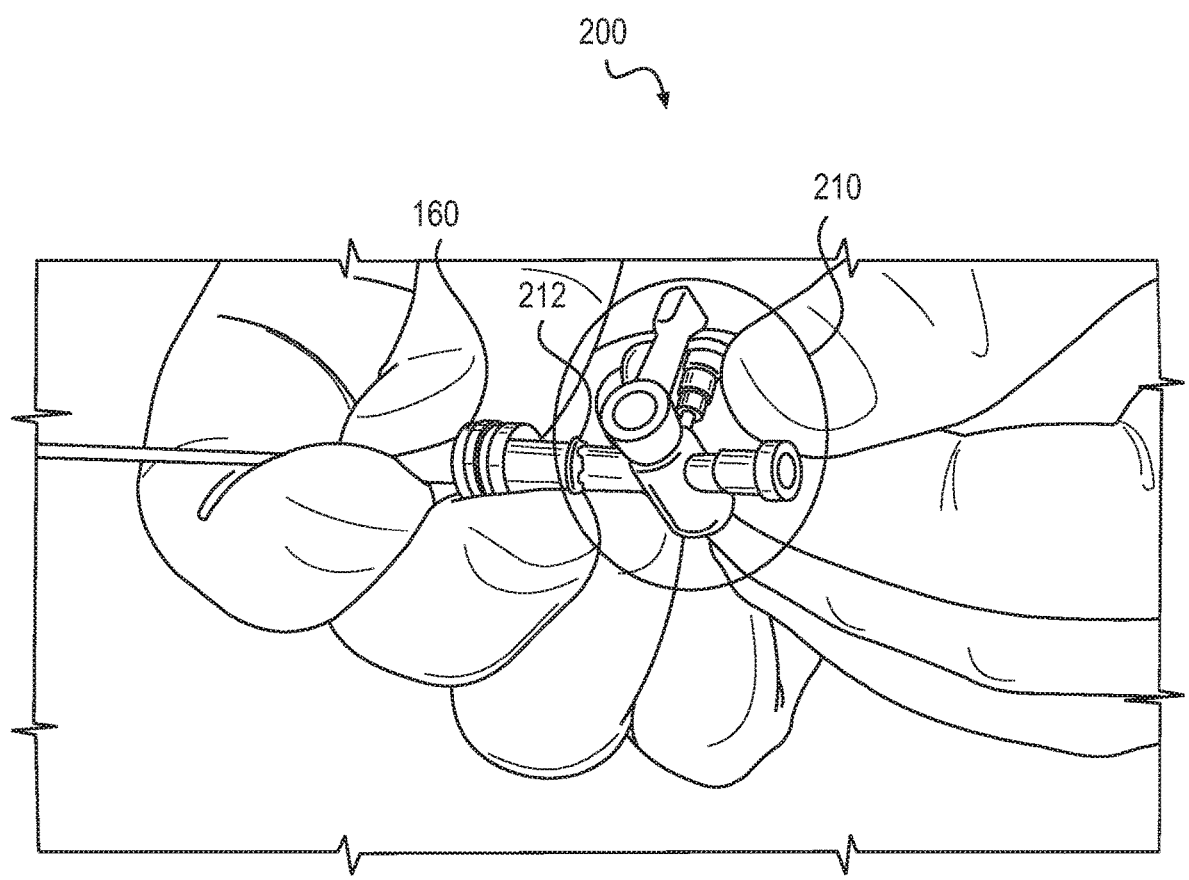
FIGS. 2A-2C depict the steps to assemble the components for the fluid collection portion of the collection system.

FIG. 2A illustrates the connection of the blunt tip needle 160 to a three-way stopcock 210 (circled) at connection 212.

Figure 2B:
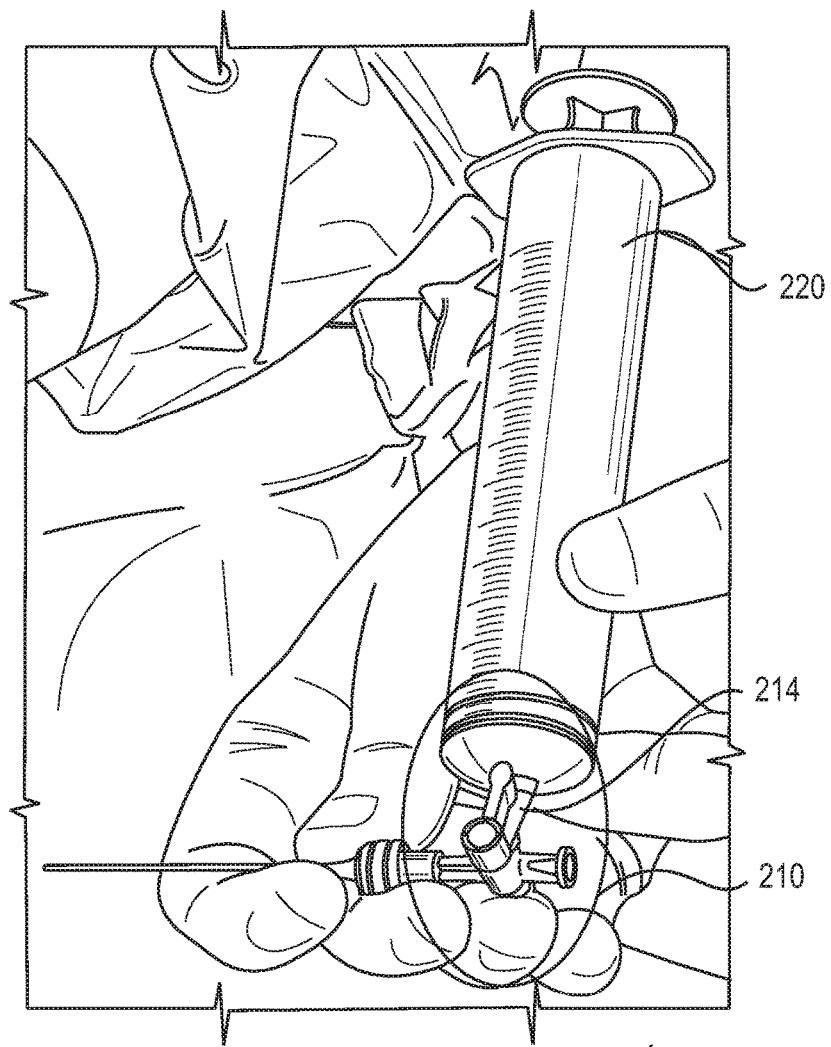

FIG. 2B illustrates the connection of a 60 cc Luer lock syringe 220 connected to the three-way stopcock at the Luer Lock connection 214. The syringe is utilized to clear any obstruction in the tubing 230 (see FIG. 2C).

Figure 2C:
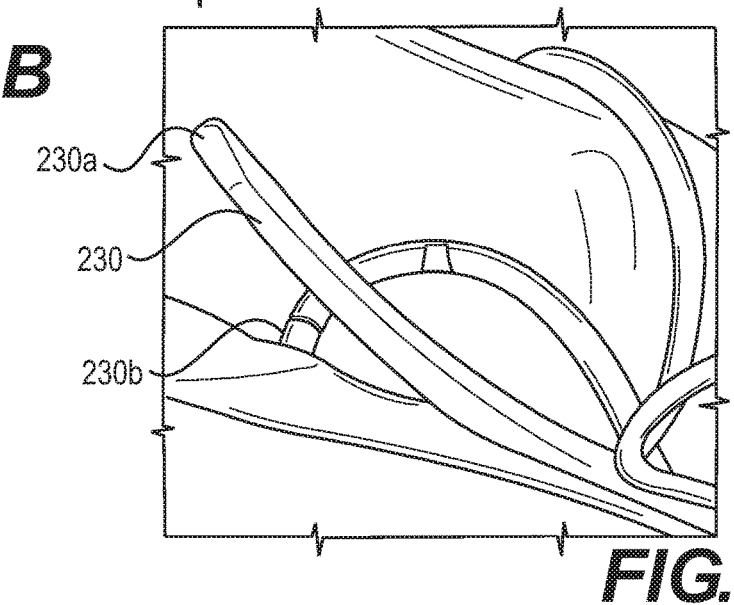

FIG. 2C shows a length of sterile tubing 230 with a first end 230a and a second end 230b. The first end is connected to the three-way stopcock 210 at connection 214. This arrangement with the syringe allows the amniotic fluid to be collected sterilely through the blunt tip needle 160 and sterile tubing 230 to a collection container 300 (see FIG. 3A) under ultrasound 150 guidance.

Figure 3A:
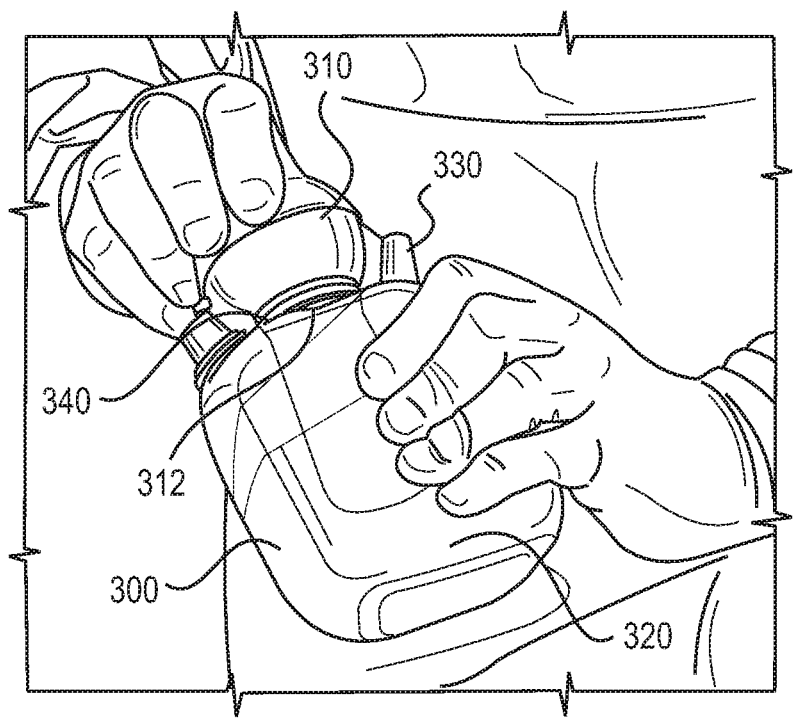
FIGS. 3A-3D depict the steps to prepare the container for collection of the amniotic fluid and to attach the assembled needle portion thereto.

FIG. 3A shows a sterile collection container 300 with a collection volume of about 400 cc to about 800 cc for sterile collection of the amniotic fluid specimen. The collection container comprises a pump with a low suction device 310 or spring loaded low suction device and an internal balloon 320 fluidly connected to the suction device at 312. The collection container comprises an inlet 330 and a vent 340 having a cap 342 (see FIG. 3B).

Figure 3B:
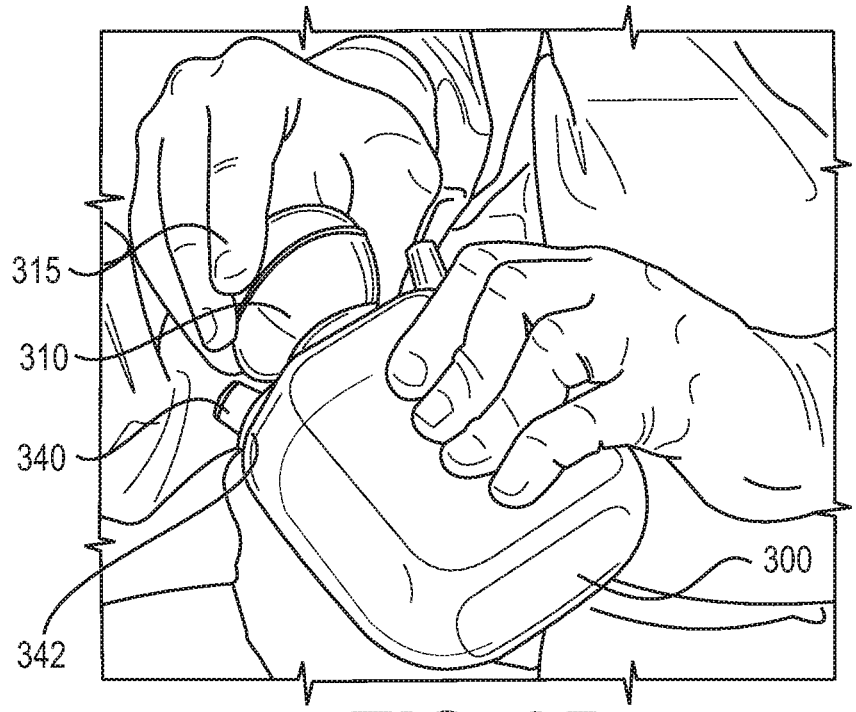

FIG. 3B demonstrates manually pumping up at 315 the internal balloon 320 in the sterile collection container 300 with the low suction device 310 which allows a low level suction for more efficient sterile collection of the amniotic fluid specimen. The cap 342 to the vent 340 is removed during pumping.

Figure 3C:
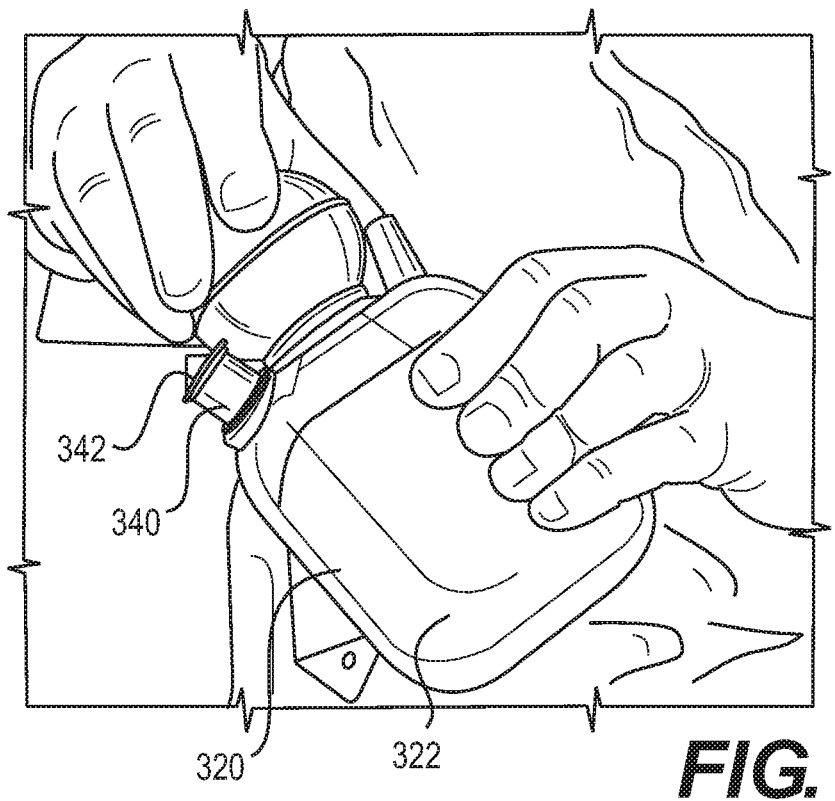

FIG. 3C shows the internal balloon 320 fully expanded at 322. Once maximum suction is obtained by full expansion of the internal balloon the vent 340 is resealed with the cap 342.

Figure 3D:
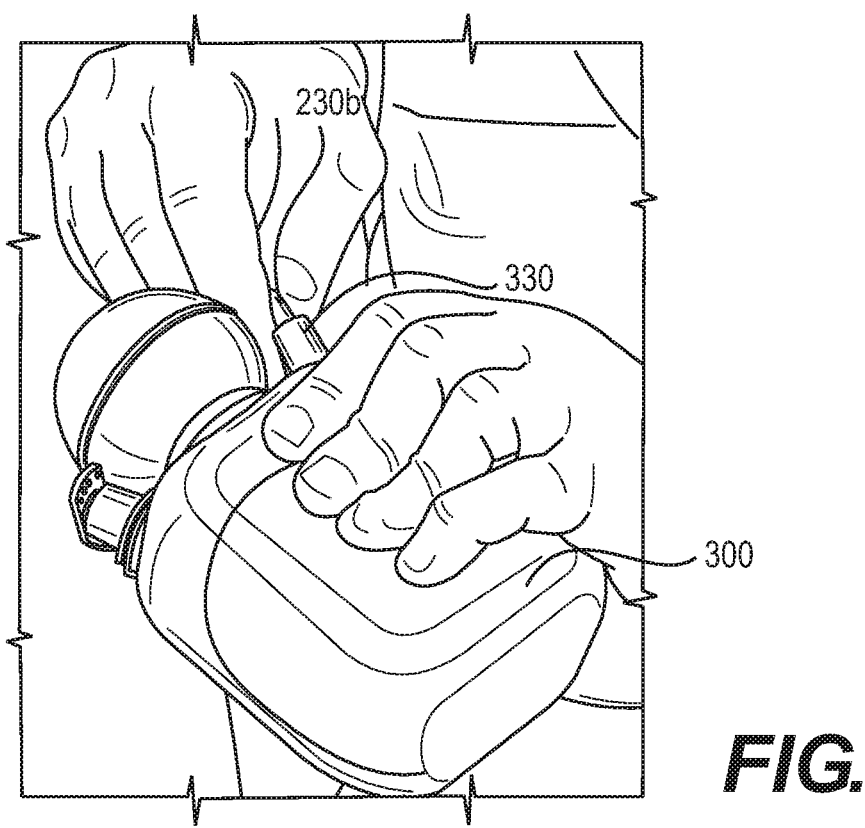

FIG. 3D demonstrates connecting the second end 230b of the tubing 230 to the inlet 330 of the collection container 300.

Figure 4:
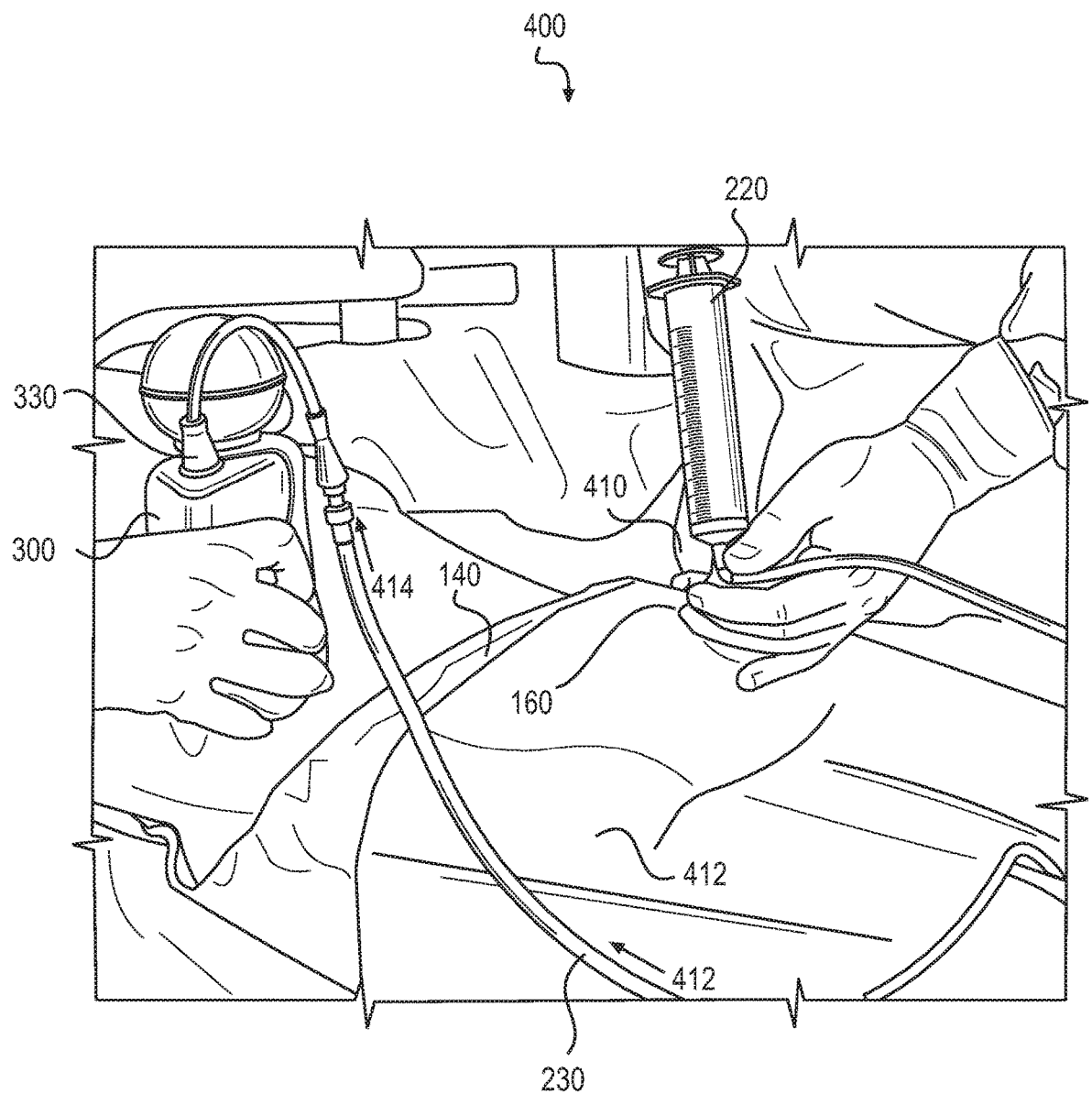
FIG. 4 depicts the assembled collection system.

FIG. 4 illustrates the fully connected collection system 400 which can now be utilized to obtain the sterile amniotic fluid from the patient. The low level suction in the inflated internal balloon 320 assists in drawing the amniotic fluid through the blunt tip needle 160 at 410 upon its ultrasound guided insertion into incision 140, through the tubing 230 at 412 and into the sterile collection container 300 via inlet 330 at 414. The syringe 220 is useful to remove a blockage, for example air, from the tubing if it occurs and keeps the collection system closed. The collection container can be placed on the floor to improve gravity drainage in addition to the low suction of the collection device.

Figure 5:
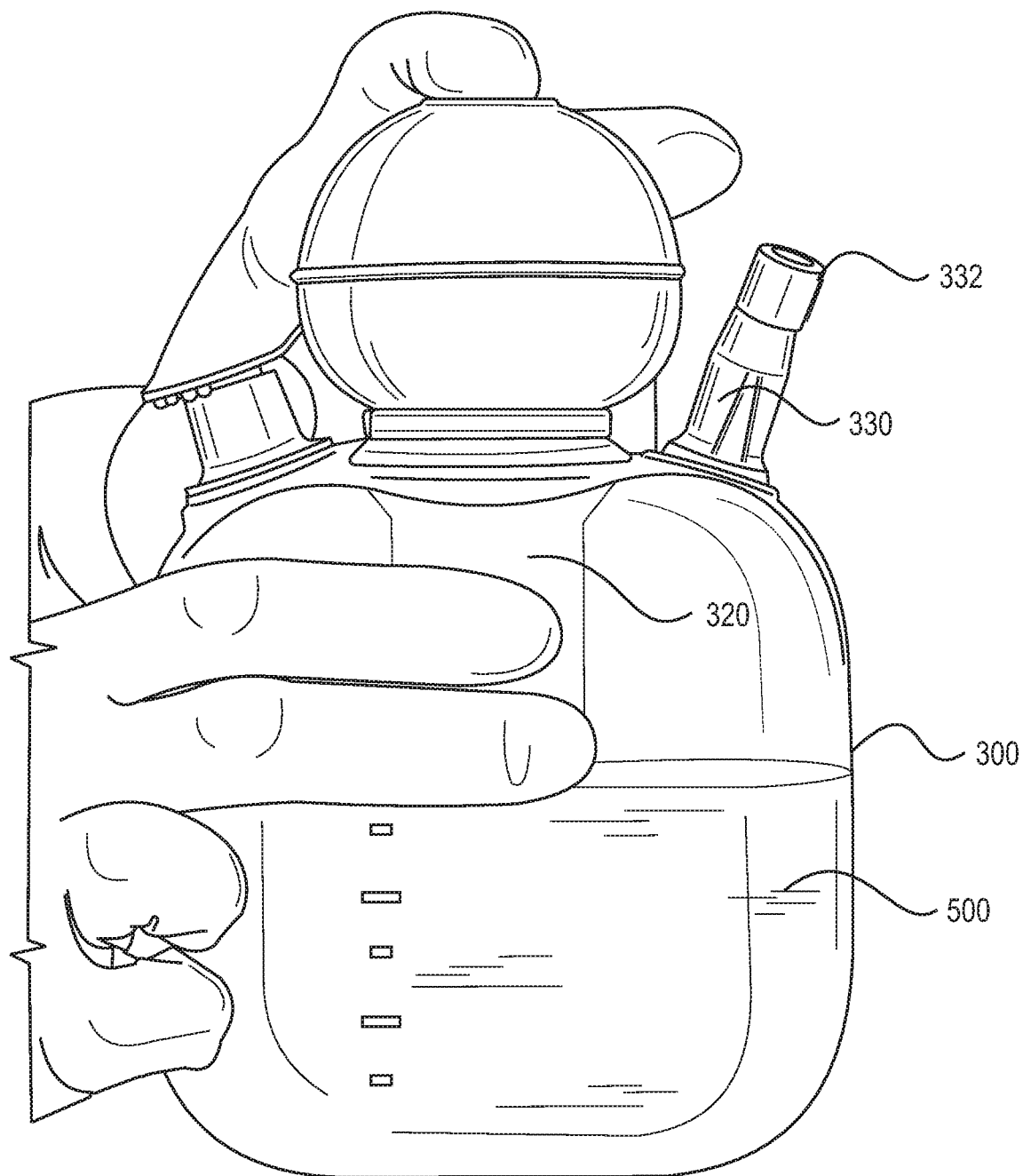
FIG. 5 depicts the sealed collection container with the amniotic fluid.

FIG. 5 shows the sterile connection container 300 after the amniotic fluid 500 collection is completed. A sterile top 332 seals the inlet 330 after the tubing 230 (see FIG. 4) has been removed. As the amniotic fluid is collected, the internal balloon 320 deflates. The completely closed sterile collection container is now ready to be refrigerated and shipped to a processing facility.

Figure 6A:
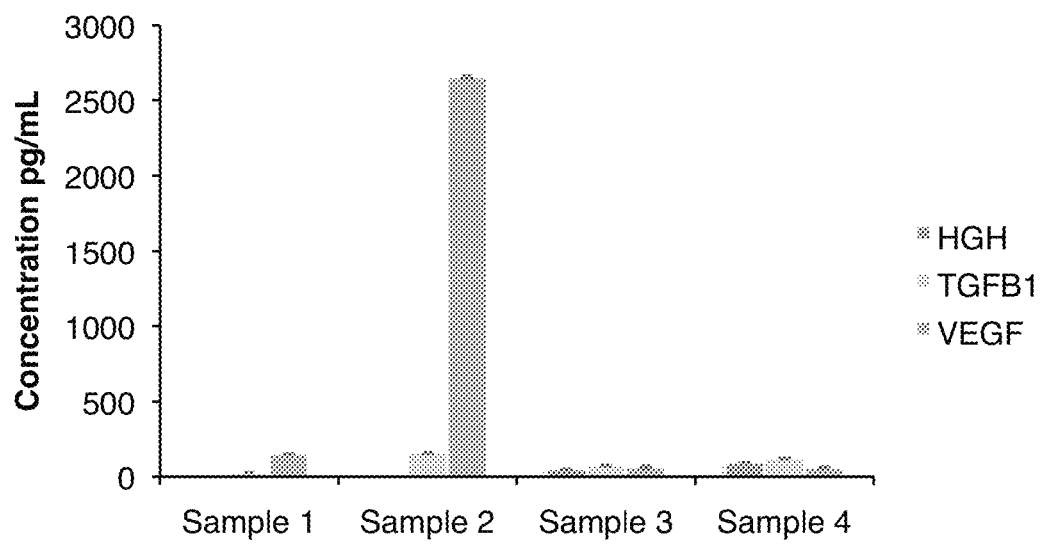
FIG. 6A shows the concentrations of human growth hormone, transforming growth factor beta 1 and vascular endothelial growth factor in sterilely filtered human amniotic fluid from four samples.
Figure 6B:
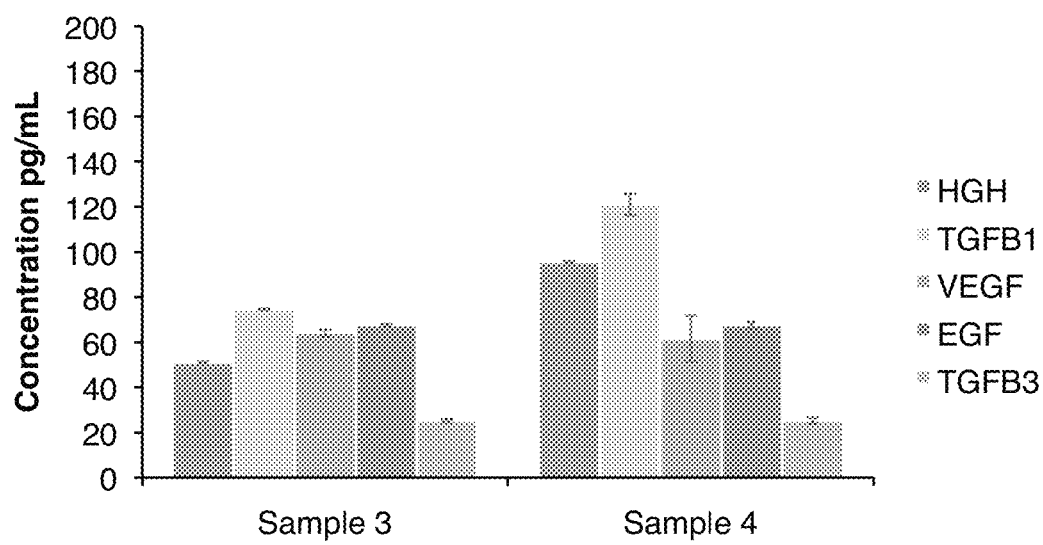
FIG. 6B shows the concentrations of human growth hormone, transforming growth factor beta 1, vascular endothelial growth factor, epidermal growth factor, transforming growth factor beta 3 in sterilely filtered human amniotic fluid from two samples.

FIGS. 6A-6B show the concentrations of growth factors in the sterilely filtered human amniotic fluid. Samples are taken from the sterilely filtered human amniotic fluid. The concentrations of human growth hormone, transforming transforming growth factor beta 1, vascular endothellal growth factor, epidermal growth factor, transforming growth factor beta 3 are measured. The result shows that the concentration of vascular endothellal growth factor in sample 2 is about 2500 pg/mL while all the other concentrations of the growth factors in the four samples are in the range of 30-150 pg/mL.

Figure 7:
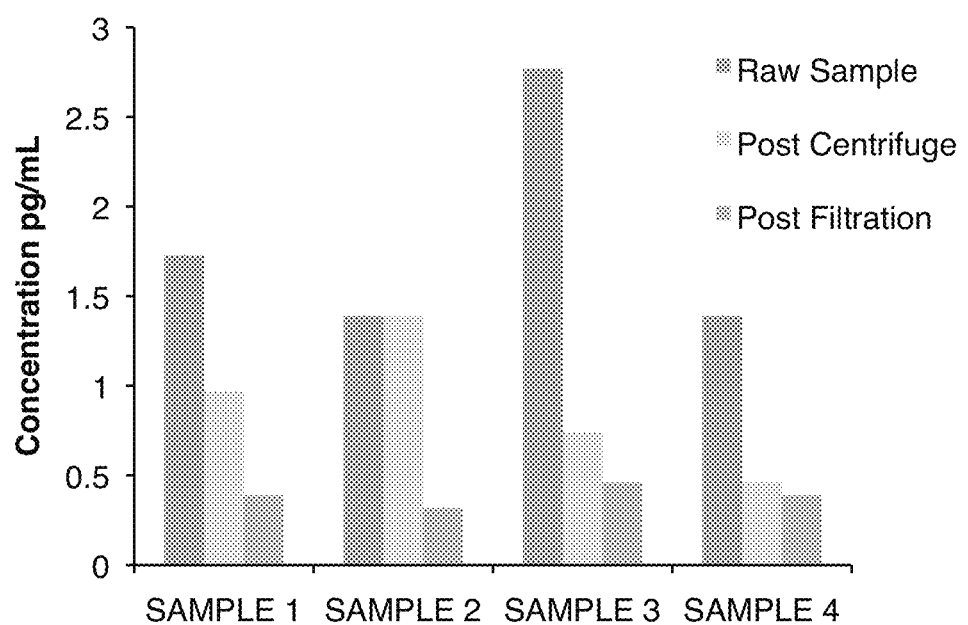
FIG. 7 shows the concentrations of growth differentiation factor 11 before the centrifugation, post centrifugation and post filtering.

FIG. 7 shows the concentration variations of growth differentiation factor before centrifugation, post centrifugation and post filtration. The results indicate that after centrifugation, about 27% to about 100% growth differentiation factor from the raw amniotic fluid is retained and after the filtration about 17% to about 29% growth differentiation factor from raw amniotic fluid is retained.

EXAMPLE 1

Human amniotic fluid is collected from selected caesarean sections, which make aspiration of the amniotic fluid in clean condition possible. Then the amniotic fluid is stored in refrigerated condition at 2° C. to 6° C. before the clarification and filtration process. The amniotic fluid is centrifuged at 5,000 to 10,000 rpm for 30 minutes to 1 hour in 50 mL to 250 mL swing out buckets. The supernatant is collected. When collecting the supernatant it is important to avoid detaching or aspirating insoluble components possibly coming from the pellet or from the fatty overlayer. If the supernatant still contains residual insoluble components, it may be pre-filtered with 5 to 10 μm cellulose esters capsule pre-filters without Triton surfactant to avoid contamination in the filtration process. The liquid phase is collected and filtered with poly ether sulfone 1.0 μm capsule filters and the liquid is collected. The liquid is then filtered with poly ether sulfone 0.2 μm capsule filter. The filtrate is transferred to vials and sealed with stoppers aseptically. Four samples from the final filtrate are taken to test whether the sterile filtered human amniotic fluid retains growth factors, such as human growth hormone, transforming growth factor beta 1, vascular endothellal growth factor, epidermal growth factor, transforming growth factor beta 3.

The results in FIG. 6A shows that the four specimens retains the growth factors. The concentration of the growth factor in the sterile filtered amniotic fluid is from about 30 pg/mL to about 2500 pg/mL. Except the vascular endothellal growth factor in sample 2, the concentrations of all the factors in the four samples are in the range of 30-150 pg/mL. These results demonstrate that the method to sterile filter human amniotic fluid described in the present invention retains the growth factors in the amniotic fluid, which are necessary for regenerative healing process.

EXAMPLE 2

Human amniotic fluid was collected from selected caesarean sections, which make aspiration of the amniotic fluid in clean conditions possible. Then the amniotic fluid is stored in refrigerated condition at 2° C. to 6° C. for less than 72 hours, before the clarification and filtration process. The amniotic fluid is centrifuged at 5,000 to 10,000 rpm for 30 minutes to 1 hour in 50 mL to 250 mL swing out buckets. The supernatant is collected and filtered with poly ether sulfone 1.0 μm capsule filters.

The liquid is collected and then filtered with poly ether sulfone 0.2 μm capsule filter. The filtrate is transferred to vials and sealed with stoppers aseptically.

Four samples are taken. In each sample, the concentrations of growth differentiation factor 11 before the centrifugation, after centrifugation and after filtering are measured. The results are plotted in FIG. 7. It is shown that although part of growth differentiation factor 11 are lost in centrifugation and filtration process, the final sterile filtered amniotic fluid still retains about 17% to 29% of growth differentiation factor from the raw human amniotic fluid.

EXAMPLE 3

The amniotic fluid from the final filtration is aseptically transferred to syringes or vials, then kept in a deep freezer at about −80° C. to about −20° C. for long term storage.

The sterile amniotic fluid is dried in the vial via lyophilization in a built-in a sterile environment. The lyophilisate derived from the amniotic fluid is reconstituted with sterile water before its injection or topical administration. The lyophilisate can be stored at from +4° C. to about +25° C. (room temperature). All of this operation may be carried out in sterile condition and does not need additional sterilization methods such as a final irradiation.

If needed, the lyophilisate derived from amniotic fluid through lyophilization may be irradiated by e-beam irradiation or gamma ray irradiation to add another guarantee for the final sterility of the powder. Irradiation of a lyophilisate is much less denaturing for proteins and peptides than irradiating aqueous solutions, because the absence of water considerably reduces the production of reactive superoxide anions and their diffusion during irradiation. Such superoxide anions are the main cause of splitting peptide bonds and chemically modifying amino acids of protein and peptides. After lyophilization, the amniotic fluid is reconstituted by adding the initial volume of water. After gentle homogenization, the powder is quickly dissolved in about one minute. The reconstituted amniotic liquid is transparent and may be used for wound healing, cosmetic, orthopedic, or ophthalmic applications, particularly for the treatment of dry eyes.

EXAMPLE 4

The lyophilized powder of Example 3 was dissolved in 1 mL of sterile water to reconstitute 1 mL of the initial sterile filtered amniotic fluid. Two drops were applied on each eye of ten patients suffering from the dry eye syndrome. This treatment was repeated twice per day for ten days. Two other control groups of 10 patients similarly received either their own serum or a serum prepared from cord blood as described by Kyung-Chul Yoon (Umbilical cord and its blood: A perspective on its current and potential use in Ophthalmology, in "Regenerative Medicine Using Pregnancy-Specific Biological Substances" Springer ed. 2011). 8 to 10 patients out of 10 in each group declared that they had experienced a significant benefit. For all patients, this clinical improvement was correlated with a partial or complete decrease of their initial corneal inflammation.

One skilled in the art will appreciate readily that the present invention is well adapted to carry out the objects and obtain the ends and advantages mentioned, as well as those objects, ends and advantages inherent herein. The present devices, systems and methods described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A method for obtaining sterilely filtered, cell-free, non-irradiated human amniotic fluid, the method comprising serially filtering the human amniotic fluid, the steps of the method comprising:
   collecting amniotic fluid under sterile conditions from a woman;
   removing cells, large particles and other undissolvables from the human amniotic fluid by centrifuging the human amniotic fluid to obtain clarified amniotic fluid; and
   serially filtering the clarified amniotic fluid through multiple filters selected from the group consisting of depth filters and membrane filters with a pore size of 0.45 μm and 0.2 μm to obtain a sterile filtrate that is not irradiated.

2. The method of claim 1, wherein the step of collecting amniotic fluid from a woman under sterile conditions comprises the use of an ultrasound device to provide guidance for the process of obtaining human amniotic fluid from the woman.

3. The method of claim 2, wherein the step of collecting amniotic fluid under sterile conditions comprises the use of a sterile collection container, wherein the sterile collection container comprises a pump with a suction device.

4. The method of claim 3, wherein the suction device is a low suction device or a spring loaded low suction device.

5. The method of claim 3, wherein the suction device is fluidly connected to an internal balloon.

6. The method of claim 5, further comprising manually pumping up the internal balloon in the sterile collection container using the low suction device to allow a low-level suction and collection of the amniotic fluid.

7. The method of claim 1, wherein the step of removing cells, large particles and other undissolvables from the human amniotic fluid comprises depth filtering the human amniotic fluid.

8. The method of claim 1, wherein prior to the step of filtering the clarified amniotic fluid through multiple filters selected from the group consisting of depth filters and membrane filters with a pore size of 0.45 μm and 0.2 μm, the clarified amniotic fluid is filtered through one or more filters with a pore size of between about 5 to 10 μm, and/or through one or more filters with a pore size of about 1.0 μm.

9. The method of claim 8, wherein the filters with the pore size of about 5 to 10 μm are cellulose ester filters, glass fiber filters, nylon capsule filters or nylon cartridge filters.

10. The method of claim 8, wherein the filters with the pore size of about 1.0 μm are capsule filters or cartridge filters.

11. The method of claim 8, wherein the filters with the pore size of about 1.0 μm are poly ether sulfone, poly vinylidene fluoride or cellulose acetate membrane filters.

12. The method of claim 1, wherein the filters with the pore size of 0.45 μm and 0.2 μm are capsule filters or cartridge filters.

13. The method of claim 12, wherein the filters with the pore size of 0.45 μm and 0.2 μm are poly ether sulfone, poly vinylidene fluoride or cellulose acetate membrane filters.

14. The method of claim 1, wherein the sterile filtered human amniotic fluid contains one or more of human growth hormone, transforming growth factor beta 1, vascular endothelial growth factor, epidermal growth factor, transforming growth factor beta 3, and growth differentiation factor 11.

15. The method of claim 1, further comprising lyophilizing the sterile amniotic fluid to obtain a lyophilisate thereof.

16. A sterile filtered, cell-free, non-irradiated human amniotic fluid produced by the method of claim 1.

17. A pharmaceutical formulation for wound healing, cosmetic, orthopedic or ophthalmic applications, comprising the sterile filtered, cell-free, non-irradiated amniotic fluid of claim 1.

18. A kit to obtain sterile filtered human amniotic fluid from a women using the method of claim 1, comprising:
   a three-way stopcock;
   a sterile blunt tip needle aseptically attached to the three-way stopcock;
   a luer lock syringe aseptically connected to the three-way stopcock;
   a sterile tubing aseptically connected to the three-way stopcock;
   a collection container or a collection container comprising a pump with suction device connected with the sterile tubing;
   a set of filters having a pore size of from about 5 μm to about 10 μm;

a set of capsule or cartridge filters having a pore size of about 1 μm;

a set of capsule or cartridge filters having a pore size of about 0.45 μm or/and 0.2 μm;

a set of sterile syringes or vials to store the sterile filtered amniotic fluid; and operating instructions on using the kit to obtain sterile filtered amniotic fluid.

19. The kit of claim 18, wherein the filters having the pore size of between about 5 μm to about 10 m and the capsule or cartridge filters are poly ether sulfone, poly vinylidene fluoride or cellulose acetate membrane filters.

20. The method of claim 1, where in the sterile filtered, cell-free, non-irradiated human amniotic fluid has a $10^6$ sterility assurance level.

* * * * *

UNITED STATES PATENT AND TRADEMARK OFFICE
CERTIFICATE OF CORRECTION

| | | |
|---|---|---|
| PATENT NO. | : 10,485,521 B2 | Page 1 of 1 |
| APPLICATION NO. | : 14/508578 | |
| DATED | : November 26, 2019 | |
| INVENTOR(S) | : Carl Randall Harrell | |

It is certified that error appears in the above-identified patent and that said Letters Patent is hereby corrected as shown below:

In the Claims

Claim 5, Column 10, Line 7, please replace the phrase "claim 3" with "claim 4".

Signed and Sealed this
Eighth Day of September, 2020

Andrei Iancu
*Director of the United States Patent and Trademark Office*